United States Patent
Roersma et al.

(10) Patent No.: US 8,623,002 B2
(45) Date of Patent: Jan. 7, 2014

(54) ELECTROMAGNETIC RADIATION DELIVERY APPARATUS

(75) Inventors: Michiel Errit Roersma, Eindhoven (NL); Bernardus Leonardus Gerardus Bakker, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1881 days.

(21) Appl. No.: 10/566,199

(22) PCT Filed: Jul. 20, 2004

(86) PCT No.: PCT/IB2004/051263
§ 371 (c)(1), (2), (4) Date: Jan. 25, 2006

(87) PCT Pub. No.: WO2005/009266
PCT Pub. Date: Feb. 3, 2005

(65) Prior Publication Data
US 2006/0241573 A1 Oct. 26, 2006

(30) Foreign Application Priority Data
Jul. 29, 2003 (EP) .................................... 03102328

(51) Int. Cl.
*A61B 18/18* (2006.01)

(52) U.S. Cl.
USPC ...................... 606/9; 606/10; 606/13; 607/88

(58) Field of Classification Search
USPC ...................... 606/1–15; 607/88, 89; 351/220
See application file for complete search history.

(56) References Cited

U.S. PATENT DOCUMENTS

| 5,344,434 A | 9/1994 | Talmore |
| 6,234,973 B1 * | 5/2001 | Meador et al. ................. 600/486 |
| 6,254,597 B1 * | 7/2001 | Rizoiu et al. ..................... 606/13 |
| 6,261,310 B1 * | 7/2001 | Neuberger et al. ............. 607/89 |
| 6,325,792 B1 * | 12/2001 | Swinger et al. ................... 606/4 |
| 6,508,813 B1 * | 1/2003 | Altshuler ........................... 606/9 |
| 6,662,054 B2 * | 12/2003 | Kreindel et al. .............. 607/101 |
| 6,755,849 B1 * | 6/2004 | Gowda et al. ................... 607/89 |
| 2002/0022871 A1 * | 2/2002 | Grahn et al. .................. 607/108 |
| 2002/0062142 A1 | 5/2002 | Knowlton |
| 2003/0045895 A1 * | 3/2003 | Ross et al. ..................... 606/166 |
| 2003/0045916 A1 * | 3/2003 | Anderson et al. ............... 607/89 |
| 2003/0114902 A1 * | 6/2003 | Prescott ........................ 607/89 |

(Continued)

FOREIGN PATENT DOCUMENTS

| DE | 10015787 A | 10/2001 |
| EP | 1 285 600 A1 | 2/2003 |

(Continued)

*Primary Examiner* — Bill Thomson
*Assistant Examiner* — Lynsey Crandall

(57) ABSTRACT

The present invention relates to a device for administering electromagnetic radiation to human tissue, in particular light to skin. The device comprises a treatment head with a recess (10) in which the light is emitted and in which the air pressure may be decreased by a pump (11). The device also comprises a pressure gauge (8) for measuring the pressure in the recess (10). Above a certain threshold value the device will not function, because this indicates an incorrect positioning of the device on the skin, which might cause harm to persons. By providing the pressure gauge (8), an operator may determine whether the positioning of the treatment head is correct. The device is advantageously automated in that the pressure gauge (8) is connected to control means (5) for controlling the source (3) of radiation.

16 Claims, 3 Drawing Sheets

(56) References Cited

U.S. PATENT DOCUMENTS

Figure 1A:
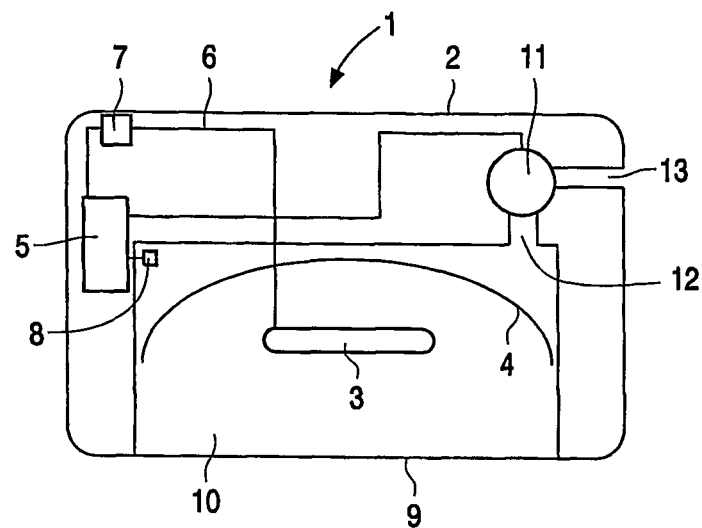

2003/0216720 A1* 11/2003 Sinofsky .................. 606/11
2004/0064167 A1* 4/2004 Berry et al. .................. 607/89
2005/0251117 A1* 11/2005 Anderson et al. .................. 606/9
2006/0241573 A1* 10/2006 Roersma et al. .................. 606/9

FOREIGN PATENT DOCUMENTS

| | | |
|---|---|---|
| JP | 1119655 U | 8/1989 |
| JP | 5096018 A | 4/1993 |
| JP | 5300912 A | 11/1993 |
| WO | 03004921 A1 | 1/2003 |

* cited by examiner

ELECTROMAGNETIC RADIATION DELIVERY APPARATUS

The present invention relates to an electromagnetic radiation delivery apparatus for skin treatment, comprising a radiation delivery head having a source of electromagnetic radiation, an emission window which is optically coupled to the source of electromagnetic radiation and is able to emit the electromagnetic radiation, and a recess which is open on one side, and vacuum means for lowering a pressure inside the recess.

Document EP 1 285 600 A1 discloses an apparatus for laser depilation. The apparatus comprises a laser diode and a suction cap surrounding the laser diode. Air may be sucked out of the suction cap. The apparatus also comprises a control unit for controlling the sucking of air and the turning on and off of the laser diode in respect of time. The apparatus is intended for use as a depilation device.

The device known from the above mentioned European patent application, and in general many devices for treatment of body parts with the aid of electromagnetic radiation, are only operated by skilled personnel. This is due to the fact that it is readily possible to supply too much radiation to the body part to be treated. Furthermore, in the case of the known apparatus, it is possible to switch on the apparatus when it is not in a correct position. It is then possible that laser radiation is emitted which hits body parts not to be treated, such as eyes or skin parts of humans or animals nearby or even other objects susceptible to being damaged by the laser radiation. This is an unsafe and undesirable situation.

There is a general tendency towards more and more unskilled persons operating such devices. Hence there is an increasing need for apparatus that may be operated in a safe way, with a lowered risk of incorrect delivery of electromagnetic radiation.

An object of the present invention is to provide an apparatus of the abovementioned type, which can be operated more safely.

The object is achieved by an electromagnetic radiation delivery apparatus of the kind mentioned in the preamble of the main claim, characterized in that the apparatus further comprises a pressure gauge for measuring a pressure inside the recess. The pressure gauge offers a simple means enabling even an unskilled operator to check whether the apparatus is applied correctly to the body part or other surface to be treated. For only if the radiation delivery head with the recess is applied correctly, a vacuum, i.e. a pressure lower than ambient pressure, may be generated. The risk of inadvertently operating the delivery apparatus is thus lowered drastically.

The vacuum gauge may be a pressure meter combined with a display, a switch or other control means. A preferred embodiment of the apparatus according to the invention is further characterized by control means connected to the pressure gauge and to the source of electromagnetic radiation, wherein the control means are able to prevent the source of electromagnetic radiation from emitting electromagnetic radiation when the pressure measured by the pressure gauge is higher than a predetermined threshold value. By thus automating the operation of the apparatus the risk of incorrect use is lowered even further. The control means may be provided as for instance an electronic switch or shutter.

If an appropriate threshold value is set, it is not possible to operate the apparatus when the pressure is above that predetermined value. Consequently, even in the case of operation by unfit people, e.g. small children, the risk of causing harm or danger is reduced. It is to be noted that in the context of the present application, "measuring" a pressure means either determining an absolute value, or determining a relative value, e.g. with respect to the predetermined threshold value. In that case it is not necessary to determine the true pressure value, but only whether the pressure is above or below the threshold value.

The threshold value, i.e. the pressure value below which the apparatus should be turned off or is automatically turned off by the control means may be appropriately selected in accordance with the properties of the body part or surface to be treated. Advantageously, the threshold value is from 10 to 250 mbar below ambient pressure. If the body part or surface to be treated is smooth, flexible and compressible, a low pressure difference may be selected, e.g. 10 or 20 mbar below ambient pressure. If the surface to be treated is rough and incompressible, the threshold value should be much lower than ambient pressure, e.g. 200 mbar, in order to ensure a correct check on the position of the radiation delivery head, since there is the possibility of air leaking into the recess even when the delivery head is in the correct position. The power of the vacuum means should then be high enough for a sufficient pressure difference to be maintained in spite of the leaking in of air.

Of course the threshold value is dependent on the ambient pressure, which means that e.g. in an area of low pressure or at a high altitude, the threshold value is correspondingly lower than the threshold value in an area of high pressure or at sea level. Generally, the threshold value depends on the ambient pressure and may be expressed as a pressure difference with ambient pressure. In the presently preferred embodiment it is possible to define the threshold value as a (negative) pressure difference with ambient pressure of between 10 and 250 mbar.

Preferably, during a period of time in which the measured pressure inside the recess is below the threshold value, the control means are able to prevent the electromagnetic radiation source from emitting electromagnetic radiation above a predetermined maximum amount of energy. By allowing only a certain maximum amount of energy to be emitted during a session, overexposure of the skin, with possible (increased) discomfort or injury may be avoided. Moreover, there will be no more uncertainty whether or not a certain part of the skin received radiation.

Another possible criterion in determining the threshold value, or in other words the pressure difference with ambient pressure, is the fact that the relatively low pressure (or high pressure difference) "sucks" the body part, in particular the skin, towards the electromagnetic radiation. Not only offers this the possibility of a controlled distance between the source of electromagnetic radiation and the body part or surface to be treated, but in the case of skin and other body parts, it also offers the advantage that the lower pressure improves the properties of those body parts for receiving radiation and responding thereto, or it may reduce unwanted side effects, as is known in the prior art.

Since the electromagnetic radiation which is delivered to the body part or surface to be treated affects said body art or surface, it may be important to limit the total amount of supplied radiation. In a preferred embodiment, the control means are able to prevent re-operation of the apparatus, thereby ensuring that it is not possible to supply more radiation energy than the predetermined maximum amount of energy without lifting the delivery head and hence breaking the vacuum.

Advantageously, the control means comprise a shutter that is able to prevent emission of the electromagnetic radiation. Such a shutter may take any desired form, e.g. an electro-optical shutter, a mechanical shutter, a switchable mirror etc.

An advantage of the presence of such a shutter is that the source of electromagnetic radiation need not be switched off when the apparatus is not to emit radiation. For many sources of electromagnetic radiation this is beneficial to the lifetime of the source. However, if frequent switching on and off of the source of electromagnetic radiation does not substantially shorten the lifetime of the source, it is also possible for the control means to simply switch the power source of the source of electromagnetic radiation, for example in the case of LED's.

In a preferred embodiment, an emission window is present in the recess. The term "emission window" relates to an area of the radiation delivery head through which electromagnetic radiation is emitted. It may come in the form of e.g. a piece of material that is transparent to the electromagnetic radiation to be emitted, e.g. glass in the case of optical light. However, it may also mean an open side of a cavity which is not covered by any material, e.g. an exit end of a tube. An advantage of an emission window being present in the recess is that when the recess is deemed to be positioned correctly, the emission window is automatically positioned correctly as well. In most cases, one emission window is present. However, it is to be noted that it is also possible for a plurality of emission windows to be present.

It is also possible for a plurality of recesses to be present. It may be contemplated that a number of small recesses is present in the form of a number of holes around the emission window. If all holes are positioned correctly, this too is a safe indication that the delivery apparatus is positioned correctly. However, preferably, a recess surrounds the emission window. This is a slightly more general instance of the case in which the emission window is present in the recess. If the recess surrounds the emission window, then an appropriate underpressure in the recess guarantees a correct positioning of the emission window. In this case the recess may come in the form of a groove around the emission window. In this way it is possible to have different shapes for the recess and the emission window. This offers advantages if the radiation is preferably supplied in a circular pattern, e.g. for homogeneity reasons, whereas a different part of the surface surrounding the part which is treated should not receive radiation. This part may of course have a different shape.

Preferably, the recess comprises a circumferential edge. In this way it is relatively simple to visually check the correct positioning by inspecting the circumferential edge.

Advantageously, the circumferential edge is flexibly deformable. This embodiment allows adaptation to a body part or surface not exactly matching the plane of the emission window or recess. Although it is possible to use a non-deformable delivery head, and to make use of the deformability of the body part or a surface to be treated, a flexibly deformable circumferential edge offers the advantage that the pressure exerted on the body part or surface differs less.

If the emission window is in the form of a transparent piece of material, this piece of material may be used to exert pressure on the body part or surface to be treated. In this case, in particular in the case of skin, the bloodstream through said body part may be affected. For instance in the case of photo hair removal, it is advantageous if the blood circulation is reduced in the tissue being treated, because then there will be less absorption of radiation by tissue parts other than the intended parts (chromophores, hair follicles). Besides, risks of possible side-effects of the treatment are reduced.

The flexibly deformable circumferential edge may be designed as a rim of resilient material such as rubber. Any other flexibly deformable material or construction is also possible.

In an advantageous embodiment, the circumferential edge lies on a plane surface, on a concave surface or on a convex surface. With these simple geometries, most body parts or other surfaces to be treated can be treated efficiently. Plane surfaces may be used for treating e.g. artificial objects or small areas of large and hence relatively flat body parts such as legs. A concave surface for the circumferential edge may be useful when treating a convex body part, e.g. a relatively small body part such as a finger or other, strongly curved body parts such as a nose. A convex surface for the circumferential edge is advantageous for the treatment of more or less concave surfaces, such as for the depilation of arm pits. In specific cases other surfaces for the circumferential edge may be even more advantageous.

In a preferred embodiment of the apparatus according to the invention, the electromagnetic radiation comprises infrared radiation, visible optical radiation or ultraviolet radiation. For the purpose of the present application, infrared radiation, visible optical radiation and ultraviolet radiation will be referred to as "optical radiation". Optical radiation is a part of the electromagnetic spectrum which is most often used for the treatment of body parts, especially by non-skilled or other private persons. In principle, however, it would be possible to use other types of electromagnetic radiation, e.g. microwave radiation or x-rays.

The preferred electromagnetic radiation according to the invention (optical radiation) covers treatments by means of heat (infrared radiation) for treatment of muscle pain, depilation, treatment of hyperbilirubinaemia, etc. by means of visible optical radiation, and artificial tanning and treatment of various skin disorders, such as vitiligo and psoriasis. Although some treatments may be performed by non-skilled or non-professional personnel, such as tanning and depilation, in many cases it may be preferable to have professional skilled personnel perform the treatment. Nevertheless, also in the case of professional personnel, the improved safety and other advantageous features of the apparatus according to the invention are valid.

Throughout the application the words "body part" and "surface to be treated" relate to any human tissue surface susceptible to a treatment by means of electromagnetic radiation. In particular this relates to skin (human skin). In general, however, any other treatable surface may be contemplated, e.g. in the field of materials research, curing of material. However, the invention has special advantages when used in relation to treatment of humans or animals, since the risks of inadvertent injury through accidents etc. are much reduced.

In the apparatus according to the present invention, the source of electromagnetic radiation may be comprised in the radiation delivery head. This means that e.g. a light source such as a LED or a high-pressure gas discharge lamp is built into the radiation delivery head. However, in an advantageous embodiment, the source of electromagnetic radiation comprises electromagnetic radiation generating means and electromagnetic radiation guiding means optically connected thereto. The presence of an electromagnetic radiation generating means and electromagnetic radiation guiding means offers the possibility of separation of these two functions. This means that a complex, large and heavy electromagnetic radiation generating means, such as a high power laser, may be present at a certain distance from the delivery head. The delivery head, which eventually emits the radiation generated by the electromagnetic radiation generating means is optically connected to the electromagnetic radiation guiding means so that the latter can guide the electromagnetic radiation to the radiation delivery head, and eventually to the emission window. This allows a relatively small and lightweight delivery head, which greatly improves the ease of use of the apparatus.

In an advantageous embodiment, the electromagnetic radiation guiding means comprise a mirror, a hollow electromagnetic radiation guide or an optical fibre. The person skilled in the art will know how to select the appropriate guiding means. E.g. in the case of a laser, an optical fiber may be the guiding means of choice. A mirror may be used in the case where a laser is the electromagnetic radiation generating means and the laser beam is used to scan a certain area to be treated. This allows said area to be illuminated homogeneously by the laser beam without the operator having to move the radiation delivery head. This greatly improves the efficacy and homogeneity of the treatment.

Advantageously, the source of electromagnetic radiation comprises a laser, a flash lamp, a LED, a gas discharge lamp or an incandescent lamp. These sources of electromagnetic radiation have proved to be efficient and useful in a wide variety of possible uses of the apparatus according to the invention. They come in a large variety of wavelengths, powers etc. Nevertheless, in particular cases, other sources may be used also, such as x-ray sources.

Figure 1B:
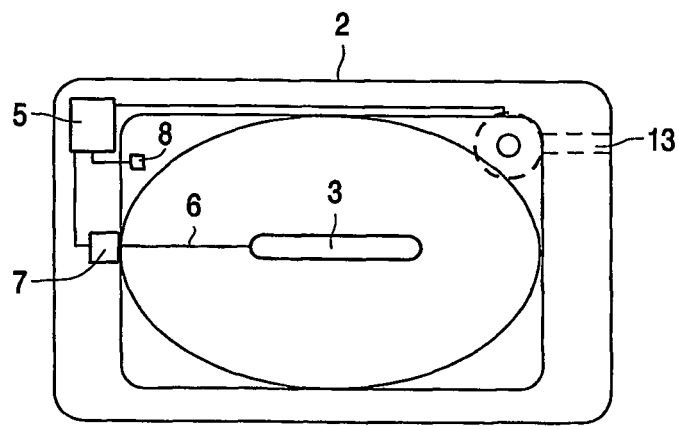
Figure 2A:
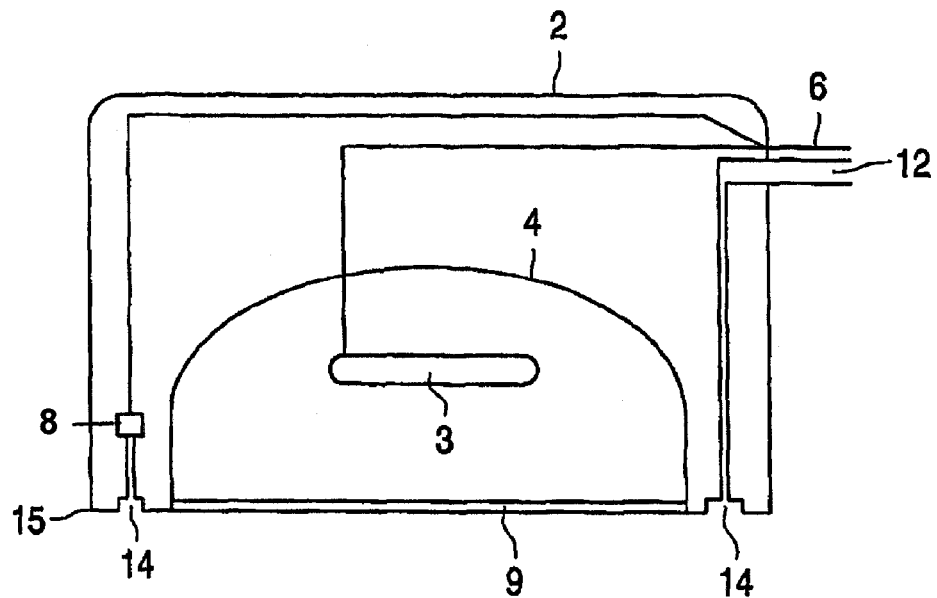
Figure 2B:
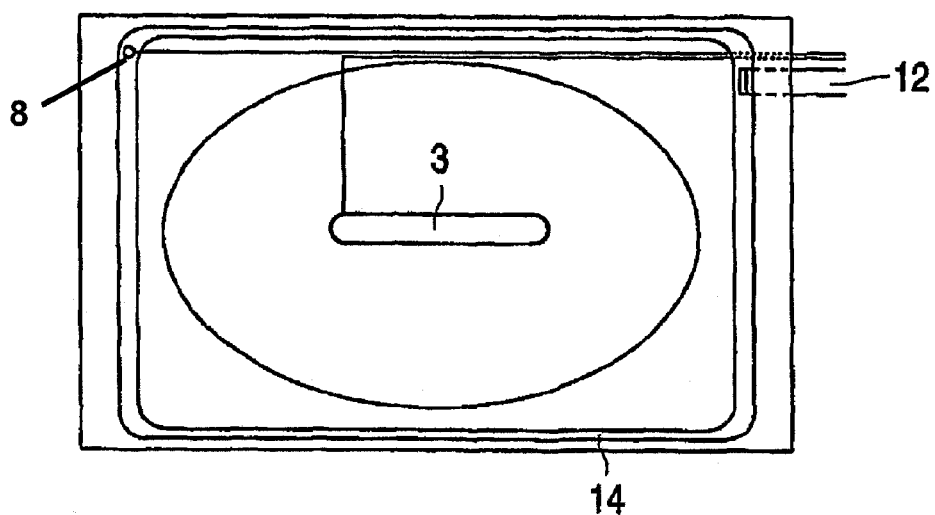
Figure 3A:
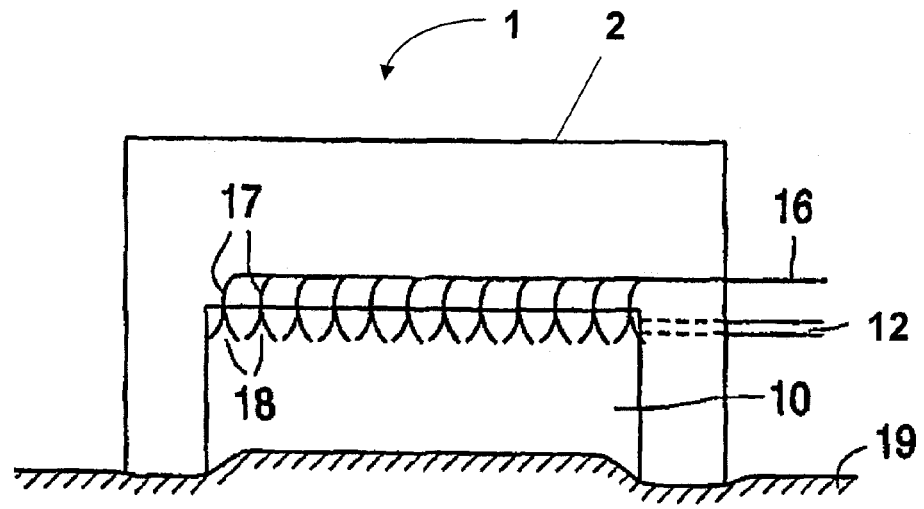
Figure 3B:
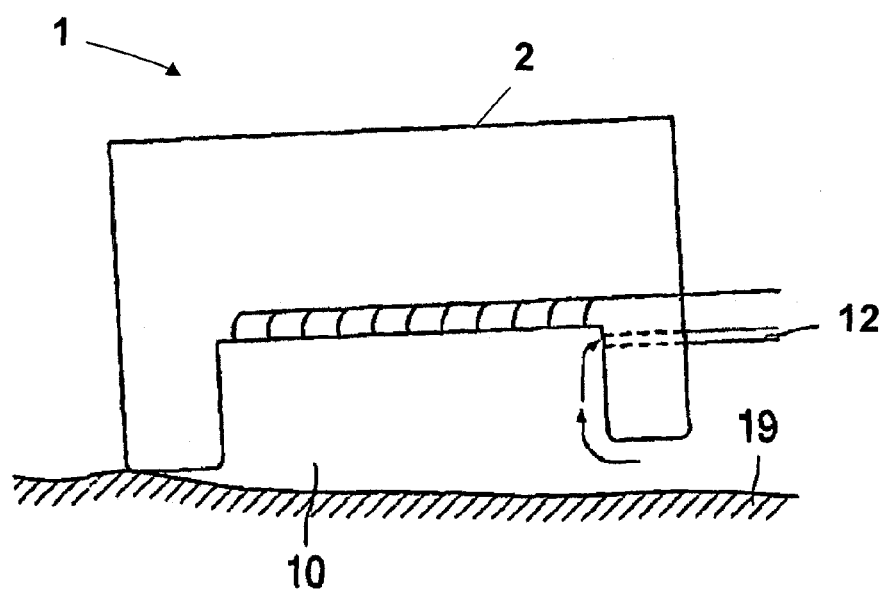

Embodiments of an electromagnetic radiation delivery apparatus in accordance with the invention will be described in detail hereafter with reference to the appended drawing, in which:

FIGS. 1a, 1b show a schematic cross-sectional view, bottom view, respectively, of a first embodiment of the device according to the invention, FIGS. 2a, 2b show a schematic cross-sectional view, bottom view, respectively, of a second embodiment of the device according to the invention, and FIGS. 3a, 3b show a schematic cross-sectional view of a third embodiment, applied correctly and incorrectly, respectively.

FIGS. 1a,b show a schematic cross-sectional view, bottom view, respectively of a first embodiment of a device 1 according to the invention. Herein, 2 is a housing for a lamp 3 and a reflector 4. Control means 5 are connected to lamp 3 via a supply cable 6, and to switch 7, and to vacuum gauge 8. An emission window 9 borders a recess 10. A vacuum pump 11 is connected to vacuum outlet 12 and to exhaust pipe 13. The device 1 comprises a treatment head which for its operation only requires a connection to the mains, or possibly only some kind of battery or other power source of its own.

The housing 2 may be made of any kind of material. Preferably a material is used which is compatible with human skin, i.e. a non-toxic, non-allergenic material, such as many plastics or metals like aluminum or steel. Optionally the materials may be coated.

The housing 2 houses a lamp 3, which may be e.g. a flash lamp, a halogen incandescent lamp or a laser, without excluding other kinds of light source. Here, as in the whole of the application, "light" refers to the part of the electromagnetic spectrum having wavelengths between about 300 nm and 1500 nm, i.e. ultraviolet to (medium wave) infrared radiation. The spectrum may be continuous or monochromatic, and the radiation may be emitted continuously or intermittently, as e.g. in a pulsed laser or a flash lamp.

Control means 5 control the operation of the lamp 3 via supply cable 6. Supply cable 6 may be a combination of an ordinary two-core electrical cable and a data cable or any other appropriate cable known in the art. Control means 5 may be embodied as ROM, a computer etc. A separate switch 7 may be supplied for actually switching the lamp 3 on and off.

The control means are also connected to a vacuum gauge 8. When the pressure signal of the vacuum gauge is such that it indicates too low a pressure difference, i.e. too high an absolute pressure, the control means either switch off or prevent the switching on of the lamp 2, or send a signal to the switch 7 to the same effect.

The vacuum gauge 8 measures the pressure inside a recess 10. The pressure inside the recess 10 is made to decrease by a pump 11, which sucks away the air inside the recess through a vacuum outlet 12 and an exhaust tube 13, which is connected to the environment. The power of the pump should preferably be selected such that the pressure inside the recess 10 drops to a value that is between about 10 and 250 mbar lower than ambient pressure. Depending on altitude and air pressure, this may correspond to an absolute pressure of between 1020 mbar and about say 600 mbar. The pressure difference should preferably not be so large that it causes discomfort to the person being treated. To this end, and also in order to be able to remove the treatment head from the skin, a valve for venting the recess is advantageously provided, either in the recess or in the vacuum means. It is to be noted that it is the pressure difference with ambient pressure which determines whether the lamp is allowed to be switched on, and also whether said safety valve should open.

The pump 11 is advantageously connected to the control means 5 in order to be switched on and off when desired. Even more advantageously, the control means may set the power of the pump 11 in order to adapt to changing ambient conditions.

The vacuum gauge 8 may be some kind of pressure difference meter which gives off an analogue or digital signal, or an absolute pressure meter. In the latter case, a desired threshold value (i.e. a value of the pressure above which the lamp should not be turned on) may be set in the pressure meter. Another possibility is that the pressure meter supplies a pressure value signal to the control means 5, which may evaluate the signal in order to decide whether or not to switch the lamp on or off.

The light from the lamp 3 is reflected by a reflector 4 towards an emission window 9, which in this case is nothing more than an opening in the housing. The emission window 9 is a connection between the recess 10, or hollow space inside the housing 2, and the environment. When the device 1 is placed correctly on the skin, the recess will be sealed tightly by the skin, so that no ambient air will enter the recess. In this case it is easy for the pump 11 to reach a sufficiently low pressure value inside the recess, i.e. below the threshold value. On the other hand, if the device is not placed correctly, air will leak into the recess, destroying the vacuum seal, and preventing the pressure inside the recess from dropping sufficiently. This will be elucidated further in the discussion of FIG. 3.

Another advantage of the sucking away of air from the recess is that any odours, debris etc. that are formed during or because of the treatment, will be sucked away as well. E.g., waste gases or cut hairs will be removed from the debris. To that end, the pump means and/or the vacuum outlet may be provided with a suitable filter. This will prevent damage to or soiling of the pump, and will ensure safe and clean removal of waste and a pleasant smell of the exhaust gas.

In this case the treatment head is the device. In other cases some parts of the device may be external to the treatment head. In particular, the treatment head is considered the part of the device with the recess and the emission window. The device as a whole consists in that case of the treatment head and the external parts, e.g. a vacuum pump and control means.

The control means 5 may be adjusted to allow only a certain amount of energy to be emitted during a single "session". In this respect, a session indicates the positioning of the treatment head on a certain spot of the skin, decreasing the air pressure to an operative value below threshold, emitting radiation, and increasing the air pressure to above threshold, in particular to ambient pressure. By allowing only a certain maximum amount of energy to be emitted during a session, overexposure of the skin, with possible (increased) discomfort or injury may be avoided. There will be no more uncertainty whether or not a certain part of the skin received radiation. The operator of the device will then be forced to lift the device and apply it again to the skin. He can then e.g. select a different area for the next treatment to avoid injury to the skin. Alternatively, e.g. in the case of treatment of deeper (skin) tissue layers, he can again apply the device to the same are of the skin, but preferably only after some time has elapsed, in order to allow the skin or other tissue parts to cool. A delay time of about 1 second or more is sufficient in most cases. Advantageously, the control means comprises means for setting a delay time, during which delay time the device is incapable of emitting radiation.

FIGS. 2a, b show a cross-sectional view, bottom view, respectively, of a second embodiment of a device according to the invention. Here, as in all drawings, similar parts will be denoted by the same reference numerals. The housing 2 again comprises a light source 3 and a reflector 4. The light source is connected to a supply cable 5. The housing comprises a circumferential recess 14 connected to a vacuum gauge 8 and a vacuum outlet 12, an emission window 9 and a circumferential edge 15. In this second embodiment, the lamp 3 is not located in the space in which the pressure will be decreased, but instead a separate space is sealed off by an emission window 9. The emission window 9 is a window of glass, a plastic, quartz etc. It may be treated to act as a filter of the radiation, e.g. by coloring the material. It may be advantageous to close off the space for the lamp, e.g. because sometimes the lamp will get very hot, produce ozone, etc., which may be dangerous to humans.

The second embodiment uses a circumferential recess 14 in order to check a correct position of the device 1 on the skin. A pressure value in the circumferential recess 14 which is lower than the threshold value will ensure a correct position of the device because the skin is a continuous surface.

In this second embodiment only a vacuum gauge 8 is present in the device (or treatment head) 1. Other parts like a pump, control means and a switch are external to the treatment head, and are connected to the relevant parts in the treatment head by means of the cable 6 and/or the vacuum outlet 12. This ensures a more light-weight and handy treatment head. It is to be noted that the vacuum gauge 8 could also be located outside the treatment head, e.g. inside the vacuum outlet near the external pump. However, it is safer to measure the pressure at the exact location where it is to be known as shown in FIGS. 1a, 1b, to prevent the risk of e.g. a blocking of the vacuum outlet between the (circumferential) recess and the vacuum gauge 8. This would simulate an incorrect actual pressure inside the recess, and lead to possibly dangerous situations.

In this case too, it is possible to ensure safe and efficient removal of waste gas, even though the circumferential recess is not connected to the space for the lamp. As soon as a correct low pressure is reached, the pump may be switched off, and the treatment may begin. After finishing the treatment, the treatment head will be lifted. At that moment, the vacuum will be broken, and the pressure will start to rise. This triggers the vacuum gauge 8 and the control means, which will switch on the pump. The pump will then suck away the gases etc. through the circumferential edge 15.

The circumferential edge 15 is simply a more "angular" version of the corresponding feature in the first embodiment. Although it might possibly be somewhat less comfortable for the person to be treated, it does ensure a safer visual check whether the device is positioned correctly on the skin. It suffices to visually check whether the edge 15 engages the skin. In a more rounded off version, this is less reliable because even in a correct position the edge which is visible from the outside need not engage the skin. It is only the lower, invisible part of the edge which must engage the skin.

FIGS. 3a, b show schematic cross-sectional views of a third embodiment of a device 1 in a correct position and an incorrect position, respectively. The device comprises a housing 2 with a recess and a vacuum outlet 12. The source of electromagnetic radiation is a fiber bundle 16 splitting up into a plurality of individual fibers 17 that each emit a bundle of radiation 18. In this case that part of the device which emits light into the recess, in particular the light emitting ends of the (optical) fibers, is considered to be the light source.

In this third embodiment even the vacuum gauge and the actual electromagnetic radiation (or "light") generating means are absent from the actual treatment head, in order for the latter to have minimum weight and dimensions. Of course, the light generating means will be optically coupled to the treatment head. E.g. the light generating means such as a laser is located in direct contact with an opposite end of the fiber bundle 16. An important advantage of this embodiment is the absence of any electrical parts in the treatment head proper, which is very safe for humans.

In FIG. 3a the treatment head is positioned correctly, i.e. such that no ambient air can enter the recess. The pump (not shown) will have no difficulty in decreasing the air pressure in the recess to a value below the threshold value. The device will work safely and can be switched on.

As can be seen in FIG. 3a, the low air pressure inside the recess may also be used to draw the skin into the recess, at least for a certain distance. This will cause the blood circulation to change favorably. It will also decrease the distance to the light sources to a certain degree.

In FIG. 3b an example is given of an incorrectly positioned device. Outside air can leak into the recess as indicated by the arrows, which prevents that the pump decreases the pressure in the recess sufficiently. Therefore the device will not be switched on, for it would not work safely because radiation might escape. Also in the case that the device is placed on a fold or other uneven part of the skin, a correct vacuum cannot be obtained, and the device will not be switched on. Of course, when during correct operation the position suddenly becomes incorrect, for instance because of an unexpected movement by the person being treated, such that the vacuum "seal" of the recess is broken, the rising air pressure will also cause the device to be turned off.

The invention claimed is:

1. An electromagnetic radiation delivery apparatus for skin treatment, the apparatus comprising:
    a housing formed around an opening;
    a source of electromagnetic radiation suspended in the opening;
    an emission window that seals the opening and is optically coupled to the source of electromagnetic radiation to emit the electromagnetic radiation;
    a circumferential recess that surrounds the emission window and creates a space that is separated from the source of electromagnetic radiation;
    a pump configured to lower a pressure inside the circumferential recess;

a pressure gauge configured to measure the pressure inside the circumferential recess; and a controller connected to the pressure gauge and to the source of electromagnetic radiation configured to control the source of electromagnetic radiation not to emit the electromagnetic radiation when the pressure measured by the pressure gauge within the circumferential recess is higher than a predetermined threshold value.

2. The apparatus according to claim 1, wherein the threshold value is from 10 to 250 mbar below ambient pressure.

3. The apparatus according to claim 1, wherein during a period of time in which the measured pressure inside the circumferential recess is below the threshold value, the controller is configured to control the electromagnetic radiation source not to emit the electromagnetic radiation above a predetermined maximum amount of energy.

4. The apparatus according to claim 1, further comprising a switch coupled to the controller and the electromagnetic radiation source, wherein the controller is configured to control the switch to prevent emission of the electromagnetic radiation.

5. The apparatus according to claim 1, wherein the circumferential recess comprises a circumferential edge.

6. The apparatus according to claim 5, wherein the circumferential edge is flexibly deformable.

7. The apparatus according to claim 5, wherein the circumferential edge is configured for use on a plane surface, on a concave surface or on a convex surface.

8. The apparatus according to claim 1, wherein the electromagnetic radiation is selected from one of infrared radiation, visible optical radiation or ultraviolet radiation.

9. The apparatus according to claim 1, wherein the source of electromagnetic radiation comprises an electromagnetic radiation generator and an electromagnetic radiation guide optically connected thereto.

10. The apparatus according to claim 9, wherein the electromagnetic radiation guide comprises a mirror, a hollow electromagnetic radiation guide or an optical fiber.

11. The apparatus according to claim 1, wherein the source of electromagnetic radiation comprises one of a laser, a flash lamp, a LED, a gas discharge lamp or an incandescent lamp.

12. The apparatus according to claim 1, further comprising a vacuum outlet coupled to the emission window and an exhaust tube coupled to the environment, wherein the pump is configured to pump air through the vacuum outlet and the exhaust tube.

13. The apparatus according to claim 1, wherein the emission window is configured to seal off the source of electromagnetic radiation from the circumferential recess.

14. The apparatus according to claim 1, wherein the controller is connected to the pump.

15. The apparatus according to claim 14, wherein the controller is configured to stop the pump when the pressure measured by the pressure gauge has reached the predetermined threshold value.

16. The apparatus according to claim 15, wherein the controller is configured to start the pump when the pressure measured by the pressure gauge rises from the predetermined threshold value to a pressure above the predetermined threshold value.

* * * * *